United States Patent
Kim et al.

(10) Patent No.: US 9,139,703 B2
(45) Date of Patent: Sep. 22, 2015

(54) METHOD OF SOLUBILIZING POORLY SOLUBLE/INSOLUBLE ACTIVE MATERIAL THROUGH FORMATION OF OLIGOMER COMPOSITE

(75) Inventors: Chul-Hwan Kim, Daejeon (KR); Seung-Hak Ko, Gunsan-si (KR); Jae-Seong Shim, Daejeon (KR); Eun-Kyoung Kwon, Daejeon (KR); Yong-Han Choi, Daejeon (KR)

(73) Assignee: BIOGENICS, INC., Daejeon (KR)

( * ) Notice: Subject to any disclaimer, the term of this patent is extended or adjusted under 35 U.S.C. 154(b) by 638 days.

(21) Appl. No.: 13/505,011

(22) PCT Filed: Oct. 15, 2010

(86) PCT No.: PCT/KR2010/007066
§ 371 (c)(1),
(2), (4) Date: Apr. 30, 2012

(87) PCT Pub. No.: WO2011/071239
PCT Pub. Date: Jun. 16, 2011

(65) Prior Publication Data
US 2012/0219604 A1  Aug. 30, 2012

(30) Foreign Application Priority Data
Dec. 9, 2009  (KR) .................. 10-2009-0121886

(51) Int. Cl.
*A61K 9/48* (2006.01)
*C08J 3/12* (2006.01)
(Continued)

(52) U.S. Cl.
CPC ............... *C08J 3/126* (2013.01); *A61K 31/00* (2013.01); *A61K 31/19* (2013.01); *A61K 31/201* (2013.01);
(Continued)

(58) Field of Classification Search
None
See application file for complete search history.

(56) References Cited

U.S. PATENT DOCUMENTS

2004/0228884 A1* 11/2004 Gupta ........................ 424/401
2006/0188578 A1*  8/2006 Fernandez et al. ......... 424/489
(Continued)

FOREIGN PATENT DOCUMENTS

KR  1020060065585  6/2006

OTHER PUBLICATIONS

Liu, Z et al, "Polysaccharides-based Nanoparticles as Drug Delivery Systems", In: Adv. Drug Deliv. Rev. Sep. 17, 2008, vol. 60, pp. 1650-1662.
(Continued)

*Primary Examiner* — Bethany Barham
*Assistant Examiner* — Dominic Lazaro
(74) *Attorney, Agent, or Firm* — IPLA P.A.; James E. Bame (57) ABSTRACT

Provided is a method of solubilizing a poorly soluble/insoluble active material through formation of an oligomer composite, in which a structure having a hydrophobic cavity structure is formed by using oligomers derived from two types of hydrophilic natural polymers and a poorly soluble/insoluble component is encapsulated in the cavity structure, and thus, self-aggregation of the poorly soluble/insoluble material is prevented and simultaneously, thermodynamic stability increases to effectively solubilize the poorly soluble/insoluble material. According to the constitution of the present invention, the method may include a first operation of preparing an oligomer composite having a cavity structure formed therein by mixing and dissolving oligomers derived from two types of hydrophilic natural polymers in water, and a second operation of adding a poorly soluble/insoluble material to the oligomer composite to encapsulate the poorly soluble/insoluble material in the hydrophobic cavity structure of the oligomer composite.

5 Claims, 1 Drawing Sheet

(51) Int. Cl.
- C08L 3/02 (2006.01)
- A61K 31/00 (2006.01)
- A61K 36/25 (2006.01)
- A61K 36/16 (2006.01)
- A61K 31/201 (2006.01)
- A61K 31/19 (2006.01)
- A61K 31/355 (2006.01)
- C07C 57/03 (2006.01)
- A61K 31/385 (2006.01)
- A61K 31/52 (2006.01)
- C08L 1/02 (2006.01)
- C08L 1/28 (2006.01)
- C08L 5/00 (2006.01)
- C08L 5/04 (2006.01)
- C08L 5/06 (2006.01)
- C08L 5/12 (2006.01)
- C08L 5/08 (2006.01)

(52) U.S. Cl.
CPC ............. *A61K 31/355* (2013.01); *A61K 31/385* (2013.01); *A61K 31/52* (2013.01); *A61K 36/16* (2013.01); *A61K 36/25* (2013.01); *C07C 57/03* (2013.01); *C08L 1/02* (2013.01); *C08L 1/286* (2013.01); *C08L 3/02* (2013.01); *C08L 5/00* (2013.01); *C08L 5/04* (2013.01); *C08L 5/06* (2013.01); *C08L 5/12* (2013.01); *C08L 5/08* (2013.01)

(56) References Cited

U.S. PATENT DOCUMENTS

2008/0102114 A1* 5/2008 Koritala et al. ............... 424/456
2008/0160096 A1* 7/2008 Berbely et al. ............... 424/493

OTHER PUBLICATIONS

Cjem, Y. et al. "Chitosan-Dextran Surfate Nanoparticles for Delivery of an Anti-angiogenesis Peptide." In: Lett. Pept. Sci. 2003, vol. 10, pp. 621-629.

Cui, Z, et al. "Chitosan-based Nanoparticles for Topical Generic Immunization" In: J. Contr, Rel. 2001, vol. 75, pp. 409-419.

Ferreira, I et al, "Encapsulation of Antioxidants by Spray-Drying" In: Chem. Eng. Trans. 2007, vol. 11, pp. 713-717.

* cited by examiner

METHOD OF SOLUBILIZING POORLY SOLUBLE/INSOLUBLE ACTIVE MATERIAL THROUGH FORMATION OF OLIGOMER COMPOSITE

CROSS-REFERENCE TO RELATED APPLICATIONS

The present application is a national stage filing of International Application No. PCT/KR2010/007066 which claims priority under 35 U.S.C. 119 and 35 U.S.C. 365 to Korean Patent Application No. 10-2009-0121886 filed on Dec. 9, 2009, which is hereby incorporated by reference in its entirety.

BACKGROUND

The present disclosure relates to a method of solubilizing a poorly soluble/insoluble active material through formation of an oligomer composite, in which a structure having a hydrophobic cavity structure is formed by using oligomers derived from two types of hydrophilic natural polymers and a poorly soluble/insoluble component is encapsulated in the cavity structure, and thus, self-aggregation of the poorly soluble/insoluble material is prevented and simultaneously, thermodynamic stability increases to effectively solubilize the poorly soluble/insoluble material.

Recently, development of natural ingredients having excellent biocompatibility and biostability as well as excellent biological activity with respect to the human body has become more important in discovering biologically active substances in cosmetics, food, and medicine industries. However, some natural ingredients are unstable under an acidic condition or others are unstable under a basic condition. That is, characteristics of the active ingredients are overall different and methods of sufficiently stabilizing active ingredients in a formulation are still in a development stage.

Therefore, natural ingredients currently having high efficacy and effect are expected to have a large potential value, but about 40% of the foregoing natural ingredients are not even in a development stage due to its low solubility. A process of increasing solubility of such a material poorly soluble in water or an aqueous solution by a certain manipulation is denoted as "solubilization". A typical technique able to improve solubility and increase absorption of drugs may include a method of using an organic solvent, such as ethanol, or surfactant as an additive, a method of preparing as a salt form when an ionization group is contained, and a method of increasing solubility by adjusting a pH, etc.

Recently, various attempts have also been made to improve typical limitations of poorly soluble/insoluble materials by introducing liposome, microemulsion, cyclodextrin, and nanopowder techniques to solubilize the poorly soluble/insoluble materials.

SUMMARY OF THE INVENTION

Embodiments provide a method of solubilizing a poorly soluble/insoluble active material through formation of an oligomer composite, in which a structure having a hydrophobic cavity structure is formed by using oligomers derived from two types of hydrophilic natural polymers and a poorly soluble/insoluble component is encapsulated in the cavity structure, and thus, self-aggregation of the poorly soluble/insoluble material is prevented and thermodynamic stability increases to effectively solubilize the poorly soluble/insoluble material.

The technical objects of the present disclosure are not limited to the aforesaid, but other technical objects not described herein will be clearly understood by those skilled in the art from descriptions below.

In one embodiment, a method of solubilizing a poorly soluble/insoluble active material through formation of an oligomer composite includes: a first operation of preparing an oligomer composite having a cavity structure formed therein by mixing and dissolving oligomers derived from two types of hydrophilic natural polymers in water; and a second operation of adding a poorly soluble/insoluble material to the oligomer composite to encapsulate the poorly soluble/insoluble material in the hydrophobic cavity structure of the oligomer composite.

In another embodiment, the method may further include, after the second operation: a third operation of removing a residual poorly soluble/insoluble material unencapsulated in the oligomer composite by filtration or centrifugation of a reaction solution; and a fourth operation of removing water and an organic solvent (when used) from the reaction solution having the residual material removed therefrom to dry.

The details of one or more embodiments are set forth in the accompanying drawings and the description below. Other features will be apparent from the description and drawings, and from the claims.

DETAILED DESCRIPTION OF THE EMBODIMENTS

Reference will now be made in detail to the embodiments of the present disclosure, examples of which are illustrated in the accompanying drawings.

A basic concept of the present invention is that when poorly soluble/insoluble materials are encapsulated in an oligomer composite having a hydrophobic cavity structure, precipitation of poorly soluble/insoluble components in an aqueous solution is prevented by preventing aggregation and re-aggregation of the poorly soluble/insoluble components, dissolution stability is improved such that a chemical reaction able to change a structure of the poorly soluble/insoluble components is not accompanied, and these components are encapsulated in an oligomer structure having a cavity structure physically formed therein to maintain an inherent natural biological activity as it is.

A method of preparing an oligomer composite according to the present invention includes: a first operation of preparing an oligomer composite having a physical cavity structure formed therein by mixing and dissolving oligomers derived from two types of hydrophilic natural polymers in water; and a second operation of adding a poorly soluble/insoluble material to the oligomer composite to encapsulate the poorly soluble/insoluble material in the hydrophobic cavity structure of the oligomer composite.

Two natural polymer oligomers are selected from the group consisting of xanthan gum, acacia gum, guar gum, arabic gum, agar, alginic acid, chitosan, pectin, carboxyalkylcellulose, maltodextrin, dextrin, and hyaluronic acid, and then mixed.

Each weight ratio of two types of the selected natural polymer oligomers with respect to distilled water is in a range of 1:1 to 1:10 and in particular, may be in a range of 1:2 to 1:4.

At this time, when the weight ratio of one natural polymer oligomer among the two types of natural polymer oligomers is too high, an encapsulation effect of a poorly soluble/insoluble active component may decrease because the hydrophobic cavity structure of the oligomer structure may not be properly formed.

Also, a weight ratio between the two types of natural polymer oligomers and water is in a range of 1:1 to 1:100. When the weight ratio of the natural polymer oligomers with respect to the water is too high, preparation of an oligomer composite solution may be difficult because viscosity of the solution may be excessively increased by the natural polymer oligomers. On the other hand, when the weight ratio of the natural polymer oligomers with respect to the water is too low, the encapsulation effect of the poorly soluble/insoluble active component may decrease because the hydrophobic cavity structure may not be properly formed due to a relatively low physical bonding force between molecules of the oligomer composite in the aqueous solution. An average molecular weight of the natural polymer oligomer used may be in a range of 1,000 to 100,000.

Also, a preparation temperature during the preparation of the oligomer composite may be within a range of 20° C. to 80° C., and in particular, the oligomer composite may be prepared within a temperature range of 40° C. to 50° C. At this time, a pH of the solution may be maintained in a range of 5 to 8. When the pH and temperature during the preparation of the oligomer composite are not controlled, the hydrophobic cavity structure may not be properly formed, because the physical bonding force between the molecules of the oligomer composite may decrease.

Meanwhile, in the second operation of adding a poorly soluble/insoluble material to the oligomer composite to encapsulate the poorly soluble/insoluble material in the hydrophobic cavity structure of the oligomer composite, the poorly soluble/insoluble material may be simply added or may be added by being dissolved in an organic solvent or the like. The poorly soluble/insoluble material is slowly added to the oligomer composite solution formed in the first operation in an amount range of 0.1 wt % to 99 wt % based on a total solid content. At this time, the poorly soluble/insoluble material may be added in an amount range of 1 wt % to 20 wt %. When the poorly soluble/insoluble material is added in an amount more than 99 wt %, an effect of improving solubility of the poorly soluble/insoluble component may decrease, because it deviates from the capacity limit of the hydrophobic cavity structure in the oligomer composite which may encapsulate the poorly soluble/insoluble component.

When the poorly soluble/insoluble material is added in the second operation, an appropriate temperature is within a range of 20° C. to 80° C., and the poorly soluble/insoluble material may be mixed and stirred within a temperature range of 40° C. to 50° C. At this time, an appropriate pH is in a range of 5 to 8 and the pH may be maintained in a range of 6.5 to 7.5. When the temperature and pH are not controlled, the poorly soluble/insoluble active component may not be properly encapsulated in the oligomer composite, because the hydrophobic cavity structure may collapse due to a decrease in the physical bonding force between the natural polymer oligomers constituting the oligomer composite.

Also, the organic solvent may be selected from the group consisting of methanol, ethanol, acetone, tetrahydrofuran (THF), and acetonitrile (AN).

The poorly soluble/insoluble materials may be selected from the group consisting of polyphenols, such as amentoflavone, ellagic acid, apigenin, berginin, diosmetin, univestin, resveratrol, isoflavones, and catechin, oily fatty acids, such as salicylic acid, alpha lipoic acid, caffeine, tocopherol, docosahexaenoic acid (DHA), eicosapentaenoic acid (EPA), and conjugated linolenic acid (CLA), and natural extracts containing a ginkgo biloba leaf extract, a red ginseng extract, and polyphenols.

Meanwhile, after the second operation, the method may further include a third operation of removing a residual poorly soluble/insoluble material unencapsulated in the oligomer composite by filtration or centrifugation of a reaction solution and a fourth operation of removing water and an organic solvent (when used) from the reaction solution having the residual material removed therefrom to dry.

The poorly soluble/insoluble materials are introduced to the oligomer composite having the cavity structure to increase the solubility of the poorly soluble/insoluble components and thus, dissolution stability may be improved.

Figure 1:
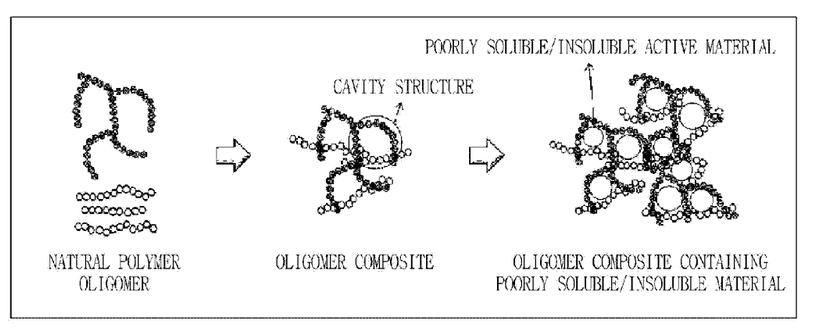
FIG. 1 illustrates a structure, in which a poorly soluble/insoluble material is encapsulated in a cavity structure of an oligomer composite of the present invention.

In the present invention, interaction between the two types of natural polymer oligomers is used to form the oligomer composite having hydrophobic cavities and thus, structural density and physical bonding strength may increase. Therefore, the solubility is improved by encapsulating a material having poorly soluble/insoluble characteristics by physical bonding. [see FIG. 1]

Hereinafter, the present invention will be described in detail, according to specific examples. However, the following examples are merely presented to exemplify the present invention, and the scope of the present invention is not limited thereto.

CONTROL GROUP EXAMPLES 1 TO 12

One type of natural polymer oligomers was selected and added to 156 g of distilled water according to a ratio of the following Table 1. A reaction temperature was maintained in a range of 40° C. to 50° C., a pH was maintained in a range of 5 to 8 by using a pH adjuster, and an oligomer aqueous solution was formed by being stirred until the oligomer was completely dissolved.

The temperature and pH of the formed oligomer aqueous solution were maintained in ranges of 40° C. to 50° C. and 6.5 to 7.5, respectively. An ellagic acid was used as a representative poorly soluble/insoluble material and a predetermined amount of the ellagic acid was slowly added to the oligomer aqueous solution. The ellagic acid was mixed and stirred within a temperature range of 40° C. to 50° C. At this time, the pH was maintained in a range of 6.5 to 7.5 to allow the ellagic acid to be completely mixed in the oligomer aqueous solution. The prepared aqueous solution was centrifuged and filtered to measure an amount of precipitates, and a filtrate was powdered by using a freeze dryer to prepare a control group.

TABLE 1

| Control Group Example | Natural polymer from which oligomer is derived | Use amount of natural polymer derived oligomer (g) | Use amount of ellagic acid (g) |
|---|---|---|---|
| Control Group Example 1 | Maltodextrin | 40 | 4 |
| Control Group Example 2 | Dextrin | 40 | 4 |
| Control Group Example 3 | Guar gum | 40 | 4 |
| Control Group Example 4 | Arabic gum | 40 | 4 |
| Control Group Example 5 | *Acacia* gum | 40 | 4 |

TABLE 1-continued

| Control Group Example | Natural polymer from which oligomer is derived | Use amount of natural polymer derived oligomer (g) | Use amount of ellagic acid (g) |
|---|---|---|---|
| Control Group Example 6 | Alginic acid | 40 | 4 |
| Control Group Example 7 | Chitosan | 40 | 4 |
| Control Group Example 8 | Carboxymethylcellulose | 40 | 4 |
| Control Group Example 9 | Pectin | 40 | 4 |
| Control Group Example 10 | Agar | 40 | 4 |
| Control Group Example 11 | Xanthan gum | 40 | 4 |
| Control Group Example 12 | Hyaluronic acid | 40 | 4 |

[Experimental Method for Evaluating Solubility and Dissolution Stability of Control Group]

The ellagic acid was added to the solutions having the natural polymer oligomers dissolved therein and mixed during the preparation of the powders of control group in Control Group Examples 1 to 12, and then the precipitates were dried during centrifugation to measure weights of insoluble precipitates.

The prepared powders of the control group were weighed and put into distilled water to make a volume of 100 ml, and aqueous solutions were then prepared by stirring for 30 minutes. The prepared aqueous solutions were put into centrifuge tubes, in which the weights thereof had been previously measured, and centrifuged. Filtrates were removed and the tubes were dried in a vacuum drier at 60° C. for five days, and amounts of precipitates were then measured by measuring weight changes and solubilities of the oligomer composites containing a poorly soluble/insoluble material with respect to water were calculated. The presence of precipitates were visually observed while the centrifuged supernatants were stored at 4° C. for zero week, one week, two weeks, three weeks, and four weeks.

The result of improvements in the solubility of poorly soluble/insoluble material and the presence of precipitates with respect to control group examples are presented in Table 2.

TABLE 2

| Control Group Example | Poorly soluble/ insoluble material | Precipitate amount during preparation of control group (g)[1] | Input amount of powders of control group during redissolution (g) | Precipitate amount during redissolution (g) | Solubility (mg/ml) | Storage period | Presence of precipitate[2] |
|---|---|---|---|---|---|---|---|
| Control Group Example 1 | Ellagic acid | 1.90 | 2.0 | 0.0 | 20.0 | 4 weeks | Occurred in one week |
| Control Group Example 2 | Ellagic acid | 1.90 | 2.0 | 0.0 | 20.0 | 4 weeks | Occurred in one week |
| Control Group Example 3 | Ellagic acid | 1.95 | 2.0 | 0.0 | 20.0 | 4 weeks | Occurred in one week |
| Control Group Example 4 | Ellagic acid | 1.94 | 2.0 | 0.0 | 20.0 | 4 weeks | Occurred in one week |
| Control Group Example 5 | Ellagic acid | 1.95 | 2.0 | 0.0 | 20.0 | 4 weeks | Occurred in one week |
| Control Group Example 6 | Ellagic acid | 1.93 | 2.0 | 0.0 | 20.0 | 4 weeks | Occurred in one week |
| Control Group Example 7 | Ellagic acid | 1.95 | 2.0 | 0.0 | 20.0 | 4 weeks | Occurred in one week |
| Control Group Example 8 | Ellagic acid | 1.96 | 2.0 | 0.0 | 20.0 | 4 weeks | Occurred in one week |
| Control Group Example 9 | Ellagic acid | 1.95 | 2.0 | 0.0 | 20.0 | 4 weeks | Occurred in one week |
| Control Group Example 10 | Ellagic acid | 1.92 | 2.0 | 0.0 | 20.0 | 4 weeks | Occurred in one week |
| Control Group Example 11 | Ellagic acid | 1.90 | 2.0 | 0.0 | 20.0 | 4 weeks | Occurred in one week |

TABLE 2-continued

| Control Group Example | Poorly soluble/ insoluble material | Precipitate amount during preparation of control group (g)[1] | Input amount of powders of control group during redissolution (g) | Precipitate amount during redissolution (g) | Solubility (mg/ml) | Storage period | Presence of precipitate[2] |
|---|---|---|---|---|---|---|---|
| Control Group Example 12 | Ellagic acid | 1.91 | 2.0 | 0.0 | 20.0 | 4 weeks | Occurred in one week |

[1] precipitate amount of ellagic acid undissolved during the preparation of single oligomer composite containing an ellagic acid
[2] storage period of 4 weeks at 4° C., observation of the presence of precipitate As shown in the result of Table 2, with respect to the control group examples in which single natural polymer oligomer was used, it may be understood that most of ellagic acid were precipitated instead of being unencapsulated in the single natural polymer oligomer during the oligomer powders containing the ellagic acid were dissolved in water and centrifuged. In order to investigate whether or not the solubilities were improved, the powders of the control group were redissolved and centrifuged, and then weights of precipitates were measured. As a result, the precipitates were not confirmed, but a residual ellagic acid was precipitated in one week when the centrifuged supernatant was stored at 4° C. and thus, it may be understood that the control group did not affect the improvement of the solubility of poorly soluble/insoluble component and the dissolution stability.

EXAMPLES 1 TO 120

Application of Oligomer Derived from Natural Polymer

Two types of natural polymer oligomers were mixed and added to 156 g of distilled water according to a ratio of the following Tables 3 to 5. A reaction temperature was maintained in a range of 40° C. to 50° C., a pH was maintained in a range of 5 to 8 by using a pH adjuster, and an oligomer composite solution was formed by stirring until the oligomers were completely dissolved.

Temperature and pH of the formed oligomer composite solution were maintained in ranges of 40° C. to 50° C. and 6.5 to 7.5, respectively. An ellagic acid was used as a representative poorly soluble/insoluble material and a predetermined amount of the ellagic acid was slowly added to the oligomer composite solution. The ellagic acid was mixed and stirred within a temperature range of 40° C. to 50° C. At this time, the pH was maintained in a range of 6.5 to 7.5 to allow the ellagic acid to be encapsulated in the hydrophobic cavity structure of the oligomer composite. The reaction solution was centrifuged and filtered to measure weight of the unencapsulated and removed ellagic acid, and a supernatant or filtrate was powdered by using a freeze dryer to prepare an ellagic acid encapsulated oligomer composite.

TABLE 3

| Example | Natural polymer from which oligomer is derived | Use amount (g) | Use amount of ellagic acid (g) |
|---|---|---|---|
| Example 1 | Xanthan gum | 10 | 4 |
|  | Maltodextrin | 30 |  |
| Example 2 | Xanthan gum | 10 | 4 |
|  | Dextrin | 30 |  |
| Example 3 | Xanthan gum | 10 | 4 |
|  | Guar gum | 30 |  |
| Example 4 | Xanthan gum | 10 | 4 |
|  | Arabic gum | 30 |  |
| Example 5 | Xanthan gum | 10 | 4 |
|  | *Acacia* gum | 30 |  |
| Example 6 | Xanthan gum | 10 | 4 |
|  | Alginic acid | 30 |  |
| Example 7 | Xanthan gum | 10 | 4 |
|  | Chitosan | 30 |  |
| Example 8 | Xanthan gum | 10 | 4 |
|  | Carboxymethylcellulose | 30 |  |
| Example 9 | Xanthan gum | 10 | 4 |
|  | Pectin | 30 |  |
| Example 10 | Xanthan gum | 10 | 4 |
|  | Agar | 30 |  |
| Example 11 | Maltodextrin | 10 | 4 |
|  | Xanthan gum | 30 |  |
| Example 12 | Maltodextrin | 10 | 4 |
|  | Dextrin | 30 |  |
| Example 13 | Maltodextrin | 10 | 4 |
|  | Guar gum | 30 |  |
| Example 14 | Maltodextrin | 10 | 4 |
|  | Arabic gum | 30 |  |
| Example 15 | Maltodextrin | 10 | 4 |
|  | *Acacia* gum | 30 |  |
| Example 16 | Maltodextrin | 10 | 4 |
|  | Alginic acid | 30 |  |
| Example 17 | Maltodextrin | 10 | 4 |
|  | Chitosan | 30 |  |
| Example 18 | Maltodextrin | 10 | 4 |
|  | Carboxymethylcellulose | 30 |  |
| Example 19 | Maltodextrin | 10 | 4 |
|  | Pectin | 30 |  |
| Example 20 | Maltodextrin | 10 | 4 |
|  | Agar | 30 |  |
| Example 21 | Dextrin | 10 | 4 |
|  | Maltodextrin | 30 |  |
| Example 22 | Dextrin | 10 | 4 |
|  | Xanthan gum | 30 |  |
| Example 23 | Dextrin | 10 | 4 |
|  | Guar gum | 30 |  |
| Example 24 | Dextrin | 10 | 4 |
|  | Arabic gum | 30 |  |
| Example 25 | Dextrin | 10 | 4 |
|  | *Acacia* gum | 30 |  |

TABLE 3-continued

| Example | Natural polymer from which oligomer is derived | Use amount (g) | Use amount of ellagic acid (g) |
|---|---|---|---|
| Example 26 | Dextrin<br>Alginic acid | 10<br>30 | 4 |
| Example 27 | Dextrin<br>Chitosan | 10<br>30 | 4 |
| Example 28 | Dextrin<br>Carboxymethylcellulose | 10<br>30 | 4 |
| Example 29 | Dextrin<br>Pectin | 10<br>30 | 4 |
| Example 30 | Dextrin<br>Agar | 10<br>30 | 4 |
| Example 31 | Guar gum<br>Maltodextrin | 10<br>30 | 4 |
| Example 32 | Guar gum<br>Dextrin | 10<br>30 | 4 |
| Example 33 | Guar gum<br>Xanthan gum | 10<br>30 | 4 |
| Example 34 | Guar gum<br>Arabic gum | 10<br>30 | 4 |
| Example 35 | Guar gum<br>*Acacia* gum | 10<br>30 | 4 |
| Example 36 | Guar gum<br>Alginic acid | 10<br>30 | 4 |
| Example 37 | Guar gum<br>Chitosan | 10<br>30 | 4 |
| Example 38 | Guar gum<br>Carboxymethylcellulose | 10<br>30 | 4 |
| Example 39 | Guar gum<br>Pectin | 10<br>30 | 4 |
| Example 40 | Guar gum<br>Agar | 10<br>30 | 4 |
| Example 41 | Arabic gum<br>Maltodextrin | 10<br>30 | 4 |
| Example 42 | Arabic gum<br>Dextrin | 10<br>30 | 4 |
| Example 43 | Arabic gum<br>Guar gum | 10<br>30 | 4 |
| Example 44 | Arabic gum<br>Xanthan gum | 10<br>30 | 4 |
| Example 45 | Arabic gum<br>*Acacia* gum | 10<br>30 | 4 |
| Example 46 | Arabic gum<br>Alginic acid | 10<br>30 | 4 |
| Example 47 | Arabic gum<br>Chitosan | 10<br>30 | 4 |
| Example 48 | Arabic gum<br>Carboxymethylcellulose | 10<br>30 | 4 |

TABLE 4

| Example | Natural polymer from which oligomer is derived | Use amount (g) | Use amount of ellagic acid (g) |
|---|---|---|---|
| Example 49 | Arabic gum<br>Pectin | 10<br>30 | 4 |
| Example 50 | *Acacia* gum<br>Maltodextrin | 10<br>30 | 4 |
| Example 51 | *Acacia* gum<br>Dextrin | 10<br>30 | 4 |
| Example 52 | *Acacia* gum<br>Guar gum | 10<br>30 | 4 |
| Example 53 | *Acacia* gum<br>Arabic gum | 10<br>30 | 4 |
| Example 54 | *Acacia* gum<br>Xanthan gum | 10<br>30 | 4 |
| Example 55 | *Acacia* gum<br>Alginic acid | 10<br>30 | 4 |

TABLE 4-continued

| Example | Natural polymer from which oligomer is derived | Use amount (g) | Use amount of ellagic acid (g) |
|---|---|---|---|
| Example 56 | *Acacia* gum<br>Chitosan | 10<br>30 | 4 |
| Example 57 | *Acacia* gum<br>Carboxymethylcellulose | 10<br>30 | 4 |
| Example 58 | *Acacia* gum<br>Pectin | 10<br>30 | 4 |
| Example 59 | *Acacia* gum<br>Agar | 10<br>30 | 4 |
| Example 60 | Alginic acid<br>Maltodextrin | 10<br>30 | 4 |
| Example 61 | Alginic acid<br>Dextrin | 10<br>30 | 4 |
| Example 62 | Alginic acid<br>Guar gum | 10<br>30 | 4 |
| Example 63 | Alginic acid<br>Arabic gum | 10<br>30 | 4 |
| Example 64 | Alginic acid<br>*Acacia* gum | 10<br>30 | 4 |
| Example 65 | Alginic acid<br>Xanthan gum | 10<br>30 | 4 |
| Example 66 | Alginic acid<br>Chitosan | 10<br>30 | 4 |
| Example 67 | Alginic acid<br>Carboxymethylcellulose | 10<br>30 | 4 |
| Example 68 | Alginic acid<br>Pectin | 10<br>30 | 4 |
| Example 69 | Alginic acid<br>Agar | 10<br>30 | 4 |
| Example 70 | Chitosan<br>Maltodextrin | 10<br>30 | 4 |
| Example 71 | Chitosan<br>Dextrin | 10<br>30 | 4 |
| Example 72 | Chitosan<br>Guar gum | 10<br>30 | 4 |
| Example 73 | Chitosan<br>Arabic gum | 10<br>30 | 4 |
| Example 74 | Chitosan<br>*Acacia* gum | 10<br>30 | 4 |
| Example 75 | Chitosan<br>Alginic acid | 10<br>30 | 4 |
| Example 76 | Chitosan<br>Xanthan gum | 10<br>30 | 4 |
| Example 77 | Chitosan<br>Carboxymethylcellulose | 10<br>30 | 4 |
| Example 78 | Chitosan<br>Pectin | 10<br>30 | 4 |
| Example 79 | Chitosan<br>Agar | 10<br>30 | 4 |
| Example 80 | Carboxymethylcellulose<br>Maltodextrin | 10<br>30 | 4 |
| Example 81 | Carboxymethylcellulose<br>Dextrin | 10<br>30 | 4 |
| Example 82 | Carboxymethylcellulose<br>Guar gum | 10<br>30 | 4 |
| Example 83 | Carboxymethylcellulose<br>Arabic gum | 10<br>30 | 4 |
| Example 84 | Carboxymethylcellulose<br>*Acacia* gum | 10<br>30 | 4 |
| Example 85 | Carboxymethylcellulose<br>Alginic acid | 10<br>30 | 4 |
| Example 86 | Carboxymethylcellulose<br>Chitosan | 10<br>30 | 4 |
| Example 87 | Carboxymethylcellulose<br>Xanthan gum | 10<br>30 | 4 |
| Example 88 | Carboxymethylcellulose<br>Pectin | 10<br>30 | 4 |
| Example 89 | Carboxymethylcellulose<br>Agar | 10<br>30 | 4 |
| Example 90 | Pectin<br>Maltodextrin | 10<br>30 | 4 |
| Example 91 | Pectin<br>Dextrin | 10<br>30 | 4 |

TABLE 4-continued

| Example | Natural polymer from which oligomer is derived | Use amount (g) | Use amount of ellagic acid (g) |
|---|---|---|---|
| Example 92 | Pectin<br>Guar gum | 10<br>30 | 4 |
| Example 93 | Pectin<br>Arabic gum | 10<br>30 | 4 |
| Example 94 | Pectin<br>*Acacia* gum | 10<br>30 | 4 |
| Example 95 | Pectin<br>Alginic acid | 10<br>30 | 4 |
| Example 96 | Pectin<br>Chitosan | 10<br>30 | 4 |

TABLE 5

| Example | Natural polymer from which oligomer is derived | Use amount (g) | Use amount of ellagic acid (g) |
|---|---|---|---|
| Example 97 | Pectin<br>Carboxymethylcellulose | 10<br>30 | 4 |
| Example 98 | Pectin<br>Xanthan gum | 10<br>30 | 4 |
| Example 99 | Pectin<br>Agar | 10<br>30 | 4 |
| Example 100 | Agar<br>Maltodextrin | 10<br>30 | 4 |
| Example 101 | Agar<br>Dextrin | 10<br>30 | 4 |
| Example 102 | Agar<br>Guar gum | 10<br>30 | 4 |
| Example 103 | Agar<br>Arabic gum | 10<br>30 | 4 |
| Example 104 | Agar<br>*Acacia* gum | 10<br>30 | 4 |
| Example 105 | Agar<br>Alginic acid | 10<br>30 | 4 |
| Example 106 | Agar<br>Chitosan | 10<br>30 | 4 |
| Example 107 | Agar<br>Carboxymethylcellulose | 10<br>30 | 4 |
| Example 108 | Agar<br>Pectin | 10<br>30 | 4 |
| Example 109 | Agar<br>Xanthan gum | 10<br>30 | 4 |
| Example 110 | Hyaluronic acid<br>Maltodextrin | 10<br>30 | 4 |
| Example 111 | Hyaluronic acid<br>Dextrin | 10<br>30 | 4 |
| Example 112 | Hyaluronic acid<br>Guar gum | 10<br>30 | 4 |
| Example 113 | Hyaluronic acid<br>Arabic gum | 10<br>30 | 4 |
| Example 114 | Hyaluronic acid<br>*Acacia* gum | 10<br>30 | 4 |
| Example 115 | Hyaluronic acid<br>Alginic acid | 10<br>30 | 4 |
| Example 116 | Hyaluronic acid<br>Chitosan | 10<br>30 | 4 |
| Example 117 | Hyaluronic acid<br>Carboxymethylcellulose | 10<br>30 | 4 |
| Example 118 | Hyaluronic acid<br>Pectin | 10<br>30 | 4 |
| Example 119 | Hyaluronic acid<br>Agar | 10<br>30 | 4 |
| Example 120 | Hyaluronic acid<br>Xanthan gum | 10<br>30 | 4 |

EXAMPLES 121 TO 138

Preparation of Oligomer Composite Containing Poorly Soluble/Insoluble Material

Dextrin and maltodextrin among natural polymer oligomers were added to distilled water according to a constant ratio as in the following Table 6. A reaction temperature was maintained in a range of 40° C. to 50° C., a pH was maintained in a range of 5 to 8 by using a pH adjuster, and an oligomer composite solution was formed by being stirred until the dextrin and maltodextrin were completely dissolved. The temperature and pH of the formed oligomer composite solution were maintained in ranges of 40° C. to 50° C. and 6.5 to 7.5, respectively. A predetermined amount of a poorly soluble/insoluble material was simply added to the oligomer composite solution or dissolved in an organic solvent to obtain a concentration of 1% to 50% and then the mixture was slowly added to the oligomer composite solution so as to allow the poorly soluble/insoluble material to be encapsulated in a hydrophobic cavity structure of the oligomer composite solution. The reaction solution was centrifuged and filtered to measure the weight of the unencapsulated and removed poorly soluble/insoluble material, an organic solvent such as ethanol was distilled by using a distiller for experimental groups including the organic solvent, and a supernatant or filtrate was powdered by using a freeze dryer to prepare an oligomer composite containing the poorly soluble/insoluble material.

TABLE 6

| Category | Use amount of dextrin (g) | Use amount of maltodextrin (g) | Name of poorly soluble/insoluble material | Added amount of poorly soluble/insoluble material (g) | Use amount of distilled water (g) |
|---|---|---|---|---|---|
| Example 121 | 10 | 30 | Amentoflavone | 4 | 156 |
| Example 122 | 10 | 30 | Diosmetin | 4 | 156 |
| Example 123 | 10 | 30 | Berginin | 10 | 150 |
| Example 124 | 10 | 30 | Univestin | 8 | 152 |
| Example 125 | 10 | 30 | Apigenin | 4 | 156 |
| Example 126 | 10 | 30 | Resveratrol | 4 | 156 |
| Example 127 | 10 | 30 | Isoflavones | 8 | 152 |
| Example 128 | 10 | 30 | Salicylic acid | 10 | 150 |
| Example 129 | 10 | 30 | Alpha lipoic acid | 8 | 152 |
| Example 130 | 10 | 30 | Caffeine | 10 | 150 |

TABLE 6-continued

| Category | Use amount of dextrin (g) | Use amount of maltodextrin (g) | Name of poorly soluble/insoluble material | Added amount of poorly soluble/insoluble material (g) | Use amount of distilled water (g) |
|---|---|---|---|---|---|
| Example 131 | 10 | 30 | Tocopherol | 8 | 152 |
| Example 132 | 10 | 30 | Docosahexaenoic acid | 8 | 152 |
| Example 133 | 10 | 30 | Eicosapentaenoic acid | 8 | 152 |
| Example 134 | 10 | 30 | Conjugated linolenic acid | 8 | 152 |
| Example 135 | 10 | 30 | *Ginkgo biloba* leaf extract | 4 | 156 |
| Example 136 | 10 | 30 | Red ginseng extract | 4 | 156 |
| Example 137 | 10 | 30 | Soybean extract | 8 | 152 |
| Example 138 | 10 | 30 | Epigallocatechin gallate | 10 | 150 |

[Experimental Method for Evaluating Solubility and Dissolution Stability of Examples]

The poorly soluble/insoluble material was added to the solutions having two types of the natural polymer oligomers dissolved therein and mixed during the preparation of the oligomer composites encapsulating the poorly soluble/insoluble materials in Examples 1 to 138, and then precipitates were dried during centrifugation or filtration to measure weights of insoluble precipitates.

Oligomer composite powders encapsulating the poorly soluble/insoluble material prepared in Examples 1 to 138 were weighed and put into distilled water to make a volume of 100 ml, and aqueous solutions were then prepared by stirring for 30 minutes. The prepared aqueous solutions were put into centrifuge tubes, in which the weights thereof had been previously measured, and centrifuged. Filtrates were removed and the tubes were dried in a vacuum drier at 60° C. for five days, and amounts of precipitates were then measured by measuring weight changes and solubilities of the oligomer composites containing a poorly soluble/insoluble material with respect to water were calculated. The presence of precipitates were visually observed while centrifuged supernatants were stored at 4° C. for zero week, one week, two weeks, three weeks, and four weeks.

The result of improvements in the solubility of the poorly soluble/insoluble material and the presence of precipitates with respect to Examples are presented in Tables 7 to 9.

TABLE 7

| Example | Poorly soluble/ insoluble material | Precipitate amount during preparation of oligomer composite (g)[1] | Input amount of oligomer composite containing a poorly soluble/insoluble material during redissolution (g) | Precipitate amount during redissolution (g) | Solubility (mg/ml) | Storage period | Presence of precipitate[2] |
|---|---|---|---|---|---|---|---|
| Example 1 | Ellagic acid | 0.03 | 2.0 | 0.0 | 20.0 | 4 weeks | No |
| Example 2 | Ellagic acid | 0.04 | 2.0 | 0.0 | 20.0 | 4 weeks | No |
| Example 3 | Ellagic acid | 0.04 | 2.0 | 0.0 | 20.0 | 4 weeks | No |
| Example 4 | Ellagic acid | 0.04 | 2.0 | 0.0 | 20.0 | 4 weeks | No |
| Example 5 | Ellagic acid | 0.04 | 2.0 | 0.0 | 20.0 | 4 weeks | No |
| Example 6 | Ellagic acid | 0.03 | 2.0 | 0.0 | 20.0 | 4 weeks | No |
| Example 7 | Ellagic acid | 0.04 | 2.0 | 0.0 | 20.0 | 4 weeks | No |
| Example 8 | Ellagic acid | 0.04 | 2.0 | 0.0 | 20.0 | 4 weeks | No |
| Example 9 | Ellagic acid | 0.04 | 2.0 | 0.0 | 20.0 | 4 weeks | No |
| Example 10 | Ellagic acid | 0.04 | 2.0 | 0.0 | 20.0 | 4 weeks | No |
| Example 11 | Ellagic acid | 0.04 | 2.0 | 0.0 | 20.0 | 4 weeks | No |
| Example 12 | Ellagic acid | 0.04 | 2.0 | 0.0 | 20.0 | 4 weeks | No |
| Example 13 | Ellagic acid | 0.03 | 2.0 | 0.0 | 20.0 | 4 weeks | No |

TABLE 7-continued

| Example | Poorly soluble/ insoluble material | Precipitate amount during preparation of oligomer composite (g)[1] | Input amount of oligomer composite containing a poorly soluble/insoluble material during redissolution (g) | Precipitate amount during redissolution (g) | Solubility (mg/ml) | Storage period | Presence of precipitate[2] |
|---|---|---|---|---|---|---|---|
| Example 14 | Ellagic acid | 0.04 | 2.0 | 0.0 | 20.0 | 4 weeks | No |
| Example 15 | Ellagic acid | 0.04 | 2.0 | 0.0 | 20.0 | 4 weeks | No |
| Example 16 | Ellagic acid | 0.04 | 2.0 | 0.0 | 20.0 | 4 weeks | No |
| Example 17 | Ellagic acid | 0.04 | 2.0 | 0.0 | 20.0 | 4 weeks | No |
| Example 18 | Ellagic acid | 0.04 | 2.0 | 0.0 | 20.0 | 4 weeks | No |
| Example 19 | Ellagic acid | 0.04 | 2.0 | 0.0 | 20.0 | 4 weeks | No |
| Example 20 | Ellagic acid | 0.04 | 2.0 | 0.0 | 20.0 | 4 weeks | No |
| Example 21 | Ellagic acid | 0.03 | 2.0 | 0.0 | 20.0 | 4 weeks | No |
| Example 22 | Ellagic acid | 0.04 | 2.0 | 0.0 | 20.0 | 4 weeks | No |
| Example 23 | Ellagic acid | 0.04 | 2.0 | 0.0 | 20.0 | 4 weeks | No |
| Example 24 | Ellagic acid | 0.04 | 2.0 | 0.0 | 20.0 | 4 weeks | No |
| Example 25 | Ellagic acid | 0.04 | 2.0 | 0.0 | 20.0 | 4 weeks | No |
| Example 26 | Ellagic acid | 0.03 | 2.0 | 0.0 | 20.0 | 4 weeks | No |
| Example 27 | Ellagic acid | 0.04 | 2.0 | 0.0 | 20.0 | 4 weeks | No |
| Example 28 | Ellagic acid | 0.04 | 2.0 | 0.0 | 20.0 | 4 weeks | No |
| Example 29 | Ellagic acid | 0.04 | 2.0 | 0.0 | 20.0 | 4 weeks | No |
| Example 30 | Ellagic acid | 0.03 | 2.0 | 0.0 | 20.0 | 4 weeks | No |
| Example 31 | Ellagic acid | 0.03 | 2.0 | 0.0 | 20.0 | 4 weeks | No |
| Example 32 | Ellagic acid | 0.04 | 2.0 | 0.0 | 20.0 | 4 weeks | No |
| Example 33 | Ellagic acid | 0.04 | 2.0 | 0.0 | 20.0 | 4 weeks | No |
| Example 34 | Ellagic acid | 0.04 | 2.0 | 0.0 | 20.0 | 4 weeks | No |
| Example 35 | Ellagic acid | 0.04 | 2.0 | 0.0 | 20.0 | 4 weeks | No |
| Example 36 | Ellagic acid | 0.04 | 2.0 | 0.0 | 20.0 | 4 weeks | No |
| Example 37 | Ellagic acid | 0.04 | 2.0 | 0.0 | 20.0 | 4 weeks | No |
| Example 38 | Ellagic acid | 0.04 | 2.0 | 0.0 | 20.0 | 4 weeks | No |
| Example 39 | Ellagic acid | 0.04 | 2.0 | 0.0 | 20.0 | 4 weeks | No |
| Example 40 | Ellagic acid | 0.03 | 2.0 | 0.0 | 20.0 | 4 weeks | No |
| Example 41 | Ellagic acid | 0.03 | 2.0 | 0.0 | 20.0 | 4 weeks | No |
| Example 42 | Ellagic acid | 0.04 | 2.0 | 0.0 | 20.0 | 4 weeks | No |
| Example 43 | Ellagic acid | 0.03 | 2.0 | 0.0 | 20.0 | 4 weeks | No |

[1] precipitate amount of a poorly soluble/insoluble material undissolved during the preparation of an oligomer composite containing a poorly soluble/insoluble material
[2] after the storage period of 4 weeks at 4° C., observation of the presence of precipitate

TABLE 8

| Example | Poorly soluble/ insoluble material | Precipitate amount during preparation of oligomer composite (g)[1] | Input amount of oligomer composite containing a poorly soluble/insoluble material during redissolution (g) | Precipitate amount during redissolution (g) | Solubility (mg/ml) | Storage period | Presence of precipitate[2] |
|---|---|---|---|---|---|---|---|
| Example 44 | Ellagic acid | 0.04 | 2.0 | 0.0 | 20.0 | 4 weeks | No |
| Example 45 | Ellagic acid | 0.04 | 2.0 | 0.0 | 20.0 | 4 weeks | No |
| Example 46 | Ellagic acid | 0.04 | 2.0 | 0.0 | 20.0 | 4 weeks | No |
| Example 47 | Ellagic acid | 0.04 | 2.0 | 0.0 | 20.0 | 4 weeks | No |
| Example 48 | Ellagic acid | 0.04 | 2.0 | 0.0 | 20.0 | 4 weeks | No |
| Example 49 | Ellagic acid | 0.04 | 2.0 | 0.0 | 20.0 | 4 weeks | No |
| Example 50 | Ellagic acid | 0.03 | 2.0 | 0.0 | 20.0 | 4 weeks | No |
| Example 51 | Ellagic acid | 0.03 | 2.0 | 0.0 | 20.0 | 4 weeks | No |
| Example 52 | Ellagic acid | 0.04 | 2.0 | 0.0 | 20.0 | 4 weeks | No |
| Example 53 | Ellagic acid | 0.04 | 2.0 | 0.0 | 20.0 | 4 weeks | No |
| Example 54 | Ellagic acid | 0.04 | 2.0 | 0.0 | 20.0 | 4 weeks | No |
| Example 55 | Ellagic acid | 0.04 | 2.0 | 0.0 | 20.0 | 4 weeks | No |
| Example 56 | Ellagic acid | 0.03 | 2.0 | 0.0 | 20.0 | 4 weeks | No |
| Example 57 | Ellagic acid | 0.04 | 2.0 | 0.0 | 20.0 | 4 weeks | No |
| Example 58 | Ellagic acid | 0.04 | 2.0 | 0.0 | 20.0 | 4 weeks | No |
| Example 59 | Ellagic acid | 0.04 | 2.0 | 0.0 | 20.0 | 4 weeks | No |
| Example 60 | Ellagic acid | 0.04 | 2.0 | 0.0 | 20.0 | 4 weeks | No |
| Example 61 | Ellagic acid | 0.03 | 2.0 | 0.0 | 20.0 | 4 weeks | No |
| Example 62 | Ellagic acid | 0.04 | 2.0 | 0.0 | 20.0 | 4 weeks | No |
| Example 63 | Ellagic acid | 0.04 | 2.0 | 0.0 | 20.0 | 4 weeks | No |
| Example 64 | Ellagic acid | 0.04 | 2.0 | 0.0 | 20.0 | 4 weeks | No |
| Example 65 | Ellagic acid | 0.04 | 2.0 | 0.0 | 20.0 | 4 weeks | No |
| Example 66 | Ellagic acid | 0.03 | 2.0 | 0.0 | 20.0 | 4 weeks | No |
| Example 67 | Ellagic acid | 0.04 | 2.0 | 0.0 | 20.0 | 4 weeks | No |
| Example 68 | Ellagic acid | 0.04 | 2.0 | 0.0 | 20.0 | 4 weeks | No |
| Example 69 | Ellagic acid | 0.04 | 2.0 | 0.0 | 20.0 | 4 weeks | No |
| Example 70 | Ellagic acid | 0.03 | 2.0 | 0.0 | 20.0 | 4 weeks | No |
| Example 71 | Ellagic acid | 0.03 | 2.0 | 0.0 | 20.0 | 4 weeks | No |
| Example 72 | Ellagic acid | 0.04 | 2.0 | 0.0 | 20.0 | 4 weeks | No |
| Example 73 | Ellagic acid | 0.04 | 2.0 | 0.0 | 20.0 | 4 weeks | No |
| Example 74 | Ellagic acid | 0.04 | 2.0 | 0.0 | 20.0 | 4 weeks | No |
| Example 75 | Ellagic acid | 0.04 | 2.0 | 0.0 | 20.0 | 4 weeks | No |
| Example 76 | Ellagic acid | 0.04 | 2.0 | 0.0 | 20.0 | 4 weeks | No |
| Example 77 | Ellagic acid | 0.04 | 2.0 | 0.0 | 20.0 | 4 weeks | No |

TABLE 8-continued

| Example | Poorly soluble/ insoluble material | Precipitate amount during preparation of oligomer composite (g)[1] | Input amount of oligomer composite containing a poorly soluble/insoluble material during redissolution (g) | Precipitate amount during redissolution (g) | Solubility (mg/ml) | Storage period | Presence of precipitate[2] |
|---|---|---|---|---|---|---|---|
| Example 78 | Ellagic acid | 0.04 | 2.0 | 0.0 | 20.0 | 4 weeks | No |
| Example 79 | Ellagic acid | 0.04 | 2.0 | 0.0 | 20.0 | 4 weeks | No |
| Example 80 | Ellagic acid | 0.03 | 2.0 | 0.0 | 20.0 | 4 weeks | No |
| Example 81 | Ellagic acid | 0.03 | 2.0 | 0.0 | 20.0 | 4 weeks | No |
| Example 82 | Ellagic acid | 0.04 | 2.0 | 0.0 | 20.0 | 4 weeks | No |
| Example 83 | Ellagic acid | 0.04 | 2.0 | 0.0 | 20.0 | 4 weeks | No |
| Example 84 | Ellagic acid | 0.04 | 2.0 | 0.0 | 20.0 | 4 weeks | No |
| Example 85 | Ellagic acid | 0.04 | 2.0 | 0.0 | 20.0 | 4 weeks | No |
| Example 86 | Ellagic acid | 0.04 | 2.0 | 0.0 | 20.0 | 4 weeks | No |
| Example 87 | Ellagic acid | 0.04 | 2.0 | 0.0 | 20.0 | 4 weeks | No |
| Example 88 | Ellagic acid | 0.04 | 2.0 | 0.0 | 20.0 | 4 weeks | No |
| Example 89 | Ellagic acid | 0.04 | 2.0 | 0.0 | 20.0 | 4 weeks | No |
| Example 90 | Ellagic acid | 0.04 | 2.0 | 0.0 | 20.0 | 4 weeks | No |
| Example 91 | Ellagic acid | 0.03 | 2.0 | 0.0 | 20.0 | 4 weeks | No |
| Example 92 | Ellagic acid | 0.04 | 2.0 | 0.0 | 20.0 | 4 weeks | No |
| Example 93 | Ellagic acid | 0.04 | 2.0 | 0.0 | 20.0 | 4 weeks | No |
| Example 94 | Ellagic acid | 0.04 | 2.0 | 0.0 | 20.0 | 4 weeks | No |
| Example 95 | Ellagic acid | 0.03 | 2.0 | 0.0 | 20.0 | 4 weeks | No |

[1] precipitate amount of a poorly soluble/insoluble material undissolved during the preparation of an oligomer composite containing a poorly soluble/insoluble material
[2] after the storage period of 4 weeks at 4° C., observation of the presence of precipitate

TABLE 9

| Example | Poorly soluble/ insoluble material | Precipitate amount during preparation of oligomer composite (g)[1] | Input amount of oligomer composite containing a poorly soluble/insoluble material during redissolution (g) | Precipitate amount during redissolution (g) | Solubility (mg/ml) | Storage period | Presence of precipitate[2] |
|---|---|---|---|---|---|---|---|
| Example 96 | Ellagic acid | 0.04 | 2.0 | 0.0 | 20.0 | 4 weeks | No |
| Example 97 | Ellagic acid | 0.04 | 2.0 | 0.0 | 20.0 | 4 weeks | No |
| Example 98 | Ellagic acid | 0.04 | 2.0 | 0.0 | 20.0 | 4 weeks | No |
| Example 99 | Ellagic acid | 0.04 | 2.0 | 0.0 | 20.0 | 4 weeks | No |
| Example 100 | Ellagic acid | 0.04 | 2.0 | 0.0 | 20.0 | 4 weeks | No |
| Example 101 | Ellagic acid | 0.03 | 2.0 | 0.0 | 20.0 | 4 weeks | No |
| Example 102 | Ellagic acid | 0.04 | 2.0 | 0.0 | 20.0 | 4 weeks | No |

TABLE 9-continued

| Example | Poorly soluble/ insoluble material | Precipitate amount during preparation of oligomer composite (g)[1] | Input amount of oligomer composite containing a poorly soluble/insoluble material during redissolution (g) | Precipitate amount during redissolution (g) | Solubility (mg/ml) | Storage period | Presence of precipitate[2] |
|---|---|---|---|---|---|---|---|
| Example 103 | Ellagic acid | 0.04 | 2.0 | 0.0 | 20.0 | 4 weeks | No |
| Example 104 | Ellagic acid | 0.03 | 2.0 | 0.0 | 20.0 | 4 weeks | No |
| Example 105 | Ellagic acid | 0.04 | 2.0 | 0.0 | 20.0 | 4 weeks | No |
| Example 106 | Ellagic acid | 0.04 | 2.0 | 0.0 | 20.0 | 4 weeks | No |
| Example 107 | Ellagic acid | 0.04 | 2.0 | 0.0 | 20.0 | 4 weeks | No |
| Example 108 | Ellagic acid | 0.04 | 2.0 | 0.0 | 20.0 | 4 weeks | No |
| Example 109 | Ellagic acid | 0.04 | 2.0 | 0.0 | 20.0 | 4 weeks | No |
| Example 110 | Ellagic acid | 0.03 | 2.0 | 0.0 | 20.0 | 4 weeks | No |
| Example 111 | Ellagic acid | 0.03 | 2.0 | 0.0 | 20.0 | 4 weeks | No |
| Example 112 | Ellagic acid | 0.04 | 2.0 | 0.0 | 20.0 | 4 weeks | No |
| Example 113 | Ellagic acid | 0.04 | 2.0 | 0.0 | 20.0 | 4 weeks | No |
| Example 114 | Ellagic acid | 0.04 | 2.0 | 0.0 | 20.0 | 4 weeks | No |
| Example 115 | Ellagic acid | 0.03 | 2.0 | 0.0 | 20.0 | 4 weeks | No |
| Example 116 | Ellagic acid | 0.04 | 2.0 | 0.0 | 20.0 | 4 weeks | No |
| Example 117 | Ellagic acid | 0.04 | 2.0 | 0.0 | 20.0 | 4 weeks | No |
| Example 118 | Ellagic acid | 0.03 | 2.0 | 0.0 | 20.0 | 4 weeks | No |
| Example 119 | Ellagic acid | 0.04 | 2.0 | 0.0 | 20.0 | 4 weeks | No |
| Example 120 | Ellagic acid | 0.04 | 2.0 | 0.0 | 20.0 | 4 weeks | No |
| Example 121 | Amentoflavone | 0.03 | 2.0 | 0.0 | 20.0 | 4 weeks | No |
| Example 122 | Diosmetin | 0.05 | 2.0 | 0.0 | 20.0 | 4 weeks | No |
| Example 123 | Berginin | 0.05 | 5.0 | 0.0 | 50.0 | 4 weeks | No |
| Example 124 | Univestin | 0.06 | 4.0 | 0.0 | 40.0 | 4 weeks | No |
| Example 125 | Apigenin | 0.03 | 2.0 | 0.0 | 20.0 | 4 weeks | No |
| Example 126 | Resveratrol | 0.03 | 2.0 | 0.0 | 20.0 | 4 weeks | No |
| Example 127 | Isoflavones | 0.06 | 4.0 | 0.0 | 40.0 | 4 weeks | No |
| Example 128 | Salicylic acid | 0.01 | 5.0 | 0.0 | 50.0 | 4 weeks | No |
| Example 129 | Alpha lipoic acid | 0.02 | 4.0 | 0.0 | 40.0 | 4 weeks | No |
| Example 130 | Caffeine | 0.00 | 5.0 | 0.0 | 50.0 | 4 weeks | No |
| Example 131 | Tocopherol | 0.01 | 4.0 | 0.0 | 40.0 | 4 weeks | No |
| Example 132 | Docosahexaenoic acid | 0.01 | 4.0 | 0.0 | 40.0 | 4 weeks | No |
| Example 133 | Eicosapentaenoic acid | 0.01 | 4.0 | 0.0 | 40.0 | 4 weeks | No |
| Example 134 | Conjugated linolenic acid | 0.01 | 4.0 | 0.0 | 40.0 | 4 weeks | No |
| Example 135 | Ginkgobiloba leaf extract | 0.02 | 2.0 | 0.0 | 20.0 | 4 weeks | No |

TABLE 9-continued

| Example | Poorly soluble/ insoluble material | Precipitate amount during preparation of oligomer composite (g)[1] | Input amount of oligomer composite containing a poorly soluble/insoluble material during redissolution (g) | Precipitate amount during redissolution (g) | Solubility (mg/ml) | Storage period | Presence of precipitate[2] |
|---|---|---|---|---|---|---|---|
| Example 136 | Red ginseng extract | 0.03 | 2.0 | 0.0 | 20.0 | 4 weeks | No |
| Example 137 | Soybean extract | 0.03 | 4.0 | 0.0 | 40.0 | 4 weeks | No |
| Example 138 | Epigalloca techin gallate | 0.01 | 5.0 | 0.0 | 50.0 | 4 weeks | No |

[1] precipitate amount of a poorly soluble/insoluble material undissolved during the preparation of an oligomer composite containing a poorly soluble/insoluble material
[2] after the storage period of 4 weeks at 4° C., observation of the presence of precipitate As shown in Tables 7 to 9, with respect to the examples using two types of the natural polymer oligomers, it may be understood that when the poorly soluble/insoluble materials were added to the oligomer composite solutions to be encapsulated and then precipitates were almost not generated during centrifugation of the reaction solutions, and most of the poorly soluble/insoluble materials were encapsulated in the oligomer composites.

Precipitates were not generated even in the case that the prepared natural polymer oligomer composite powders containing the poorly soluble/insoluble material were redissolved and centrifuged, and precipitation was not observed after storing of centrifuged supernatants at 4° C. for 4 weeks.

Thus, when the poorly soluble/insoluble materials were encapsulated through the formation of oligomer composites by using oligomers derived from two types of hydrophilic natural polymers, solubilities of the poorly soluble/insoluble materials may be improved and dissolution stability may be increased. Therefore, the poorly soluble/insoluble materials may not only be used as a functional raw material of cosmetics industry, but application thereof may also be extended to other industries (food and medicine, etc.) requiring solubilization of the poorly soluble/insoluble materials.

According to a method of solubilizing a poorly soluble/insoluble material through formation of an oligomer composite of the present invention, an oligomer structure having a hydrophobic cavity structure is formed by physical bonding between molecules and a poorly soluble/insoluble material is encapsulated in the oligomer structure. Thus, dissolution stability of the poorly soluble/insoluble material in an aqueous solution may be increased.

Also, since precipitation due to redissolution of the poorly soluble/insoluble materials is prevented, the oligomer composite encapsulating the poorly soluble/insoluble material has excellent dissolution stability, and inherent biological activity of the poorly soluble/insoluble material may also be maintained as it is, because a chemical reaction is not accompanied.

The foregoing oligomer composite encapsulating the poorly soluble/insoluble material may improve water solubility and dissolution stability of an active substance.

Since the oligomer composite encapsulating the poorly soluble/insoluble material thus prepared has excellent dissolution stability, the oligomer composite may not only be used as a functional raw material of cosmetics industry, but application thereof may also be extended to other industries (food and medicine, etc.) requiring solubilization of the poorly soluble/insoluble materials.

A method of solubilizing a poorly soluble/insoluble active material through formation of an oligomer composite according to embodiments will be described in detail with reference to the accompanying drawings. The invention may, however, be embodied in many different forms and should not be construed as being limited to the embodiments set forth herein; rather, that alternate embodiments included in other retrogressive inventions or falling within the spirit and scope of the present disclosure can easily be derived through adding, altering, and changing, and will fully convey the concept of the invention to those skilled in the art.

What is claimed is:

1. A method of solubilizing a poorly soluble/insoluble active material through formation of an oligomer composite, the method comprising:
    a first operation of preparing an oligomer composite having a hydrophobic cavity structure formed therein by mixing and dissolving oligomers derived from two types of hydrophilic natural polymers in water;
    a second operation of adding a poorly soluble/insoluble material to the oligomer composite prepared in the first operation to encapsulate the poorly soluble/insoluble material in the hydrophobic cavity structure, of the oligomer composite, which is obtained in the first operation,
    a third operation of removing a residual poorly soluble/insoluble material unencapsulated in the oligomer composite by filtration or centrifugation of a reaction solution; and
    a fourth operation of removing water and an organic solvent (when used) from the reaction solution having the residual material removed therefrom to dry,
    wherein the oligomers derived from the natural polymers are two selected from the group consisting of xanthan gum, acacia gum, guar gum, arabic gum, agar, alginic acid, pectin, carboxyalkylcellulose, maltodextrin, and dextrin,
    wherein the poorly soluble/insoluble material is any one selected from the group consisting of:
    polyphenols, wherein the polyphenols are selected from the group consisting of amentoflavone, ellagic acid, apigenin, berginin, diosmetin, univestin, resveratrol, isoflavones, and catechin;

oily fatty acids, wherein the fatty acids are selected from the group consisting of salicylic acid, alpha lipoic acid, caffeine, tocopherol, DHA (docosahexaenoic acid), EPA (eicosapentaenoic acid), and CLA (conjugated linolenic acid); and natural extracts containing a ginkgo biloba leaf extract, and a red ginseng extract.

2. The method of claim 1, wherein a weight ratio of the natural polymer oligomers with respect to a total weight of a total solid content is in a range of about 1:1 to about 1:10, and the natural polymer oligomers are mixed within a temperature range of about 20° C. to about 80° C.

3. The method of claim 1, wherein the poorly soluble/insoluble material is added in an amount range of about 0.1 wt % to about 99 wt % based on a total solid content and is mixed within a temperature range of about 20° C. to about 80° C.

4. The method of claim 1, wherein the poorly soluble/insoluble material in the second operation is added by being dissolved in an organic solvent.

5. The method of claim 4, wherein the organic solvent is any one selected from the group consisting of methanol, ethanol, acetone, THF (tetrahydrofuran), and AN (acetonitrile).

* * * * *